United States Patent [19]
Gregory

[11] Patent Number: 5,934,462
[45] Date of Patent: *Aug. 10, 1999

[54] DURABLE GLOVE PACKAGES

[76] Inventor: Duane L. Gregory, 3246 Knightswood Way, San Jose, Calif. 95148

[*] Notice: This patent issued on a continued prosecution application filed under 37 CFR 1.53(d), and is subject to the twenty year patent term provisions of 35 U.S.C. 154(a)(2).

[21] Appl. No.: 08/886,008

[22] Filed: Jul. 3, 1997

[51] Int. Cl.$^6$ .................................................. B65D 85/18
[52] U.S. Cl. ............................ 206/278; 206/484; 206/425
[58] Field of Search .................................. 206/278, 213, 206/484, 425, 438, 363, 531, 534.1, 539; 223/111

[56] References Cited

U.S. PATENT DOCUMENTS

| | | |
|---|---|---|
| D. 363,023 | 10/1995 | Taylor . |
| 2,949,181 | 8/1960 | Buccino . |
| 3,039,246 | 6/1962 | David ........................................ 206/484 |
| 3,107,786 | 10/1963 | Adelman . |
| 3,181,695 | 5/1965 | Taterka et al. . |
| 3,254,761 | 6/1966 | Hennessey et al. ...................... 206/484 |
| 3,286,831 | 11/1966 | Giberstein ................................. 206/56 |
| 3,870,150 | 3/1975 | Hummel . |
| 3,892,314 | 7/1975 | Semp . |
| 4,155,494 | 5/1979 | Poncy et al. . |
| 4,159,069 | 6/1979 | Poncy et al. . |
| 4,677,697 | 7/1987 | Hayes ....................................... 206/278 |
| 4,765,653 | 8/1988 | Fasham et al. ........................... 229/71 |
| 4,773,532 | 9/1988 | Stephenson ............................. 206/278 |
| 4,951,815 | 8/1990 | Ulbrich . |
| 4,958,728 | 9/1990 | Effendi ..................................... 206/425 |
| 5,065,863 | 11/1991 | Moyet-Ortiz et al. . |
| 5,388,699 | 2/1995 | Ratajczak et al. ....................... 206/569 |
| 5,456,354 | 10/1995 | Wood . |

Primary Examiner—David T. Fidei
Assistant Examiner—Nhan T. Lam
Attorney, Agent, or Firm—Dickstein Shapiro Morin & Oshinsky LLP

[57] ABSTRACT

A field-durable pocket-sized glove package for single-use application containing sanitary latex gloves having the capability of being dispensed one package at a time for convenient use by law enforcement personnel during field operations. The filed-durable material of the glove package has the capability of withstanding exposure to the elements, such as heat, cold, and abrasion, as well as of enduring rough treatment by law enforcement officers in the field without, before being opened, compromising the sanitary condition of the gloves inside. Further, the glove package is of convenient size for easy storage and transportation by law enforcement officers during field operations. The convenient size of the glove package may be effected by folding over the gloves at least once inside the package so that the package is pocket-sized, suitable for carrying in pockets and pouches by law enforcement personnel. Thus, the present invention provides pocket-sized glove packages made of field-durable material for single-use application by law enforcement officers in the field. The glove packages of the present invention are capable of being dispensed one package at a time, thus enabling users, such as law enforcement officers, to select and carry with them the number of packages they need for a single field operation. This dispensing feature may be effected by providing the glove packages on a glove package strip or by providing individual glove packages in a box or other container from which they can be dispensed one at a time.

13 Claims, 1 Drawing Sheet

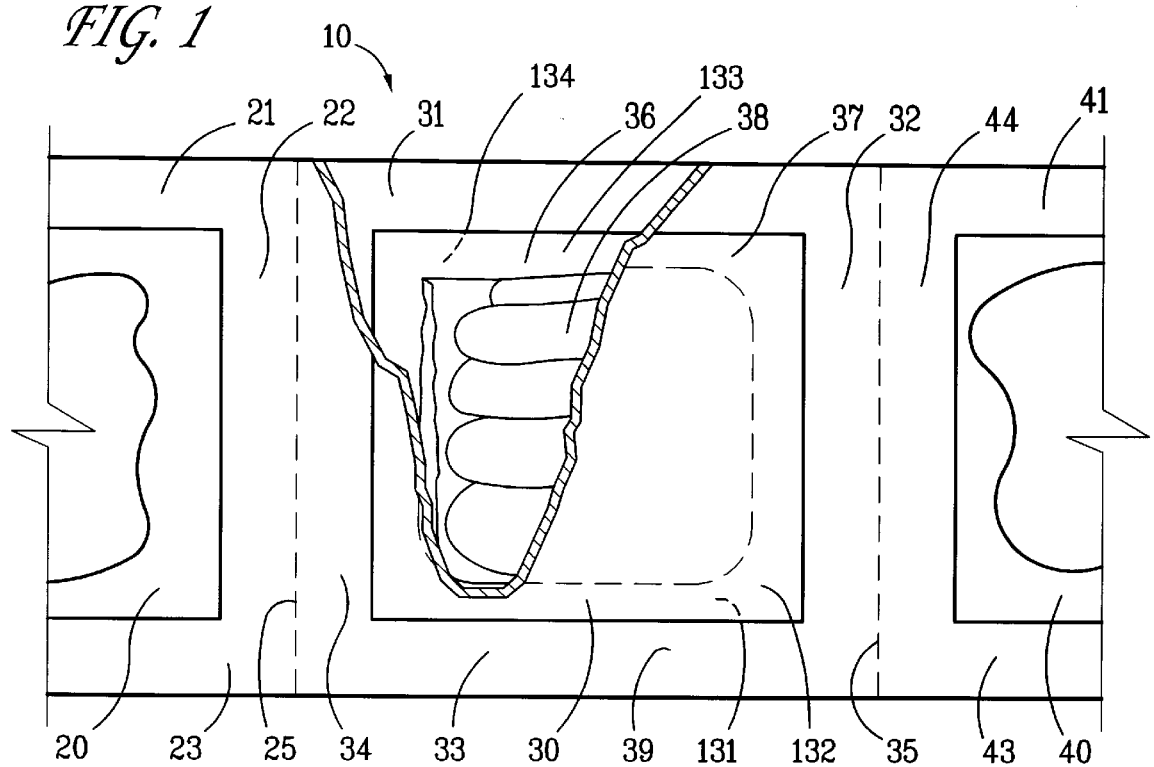
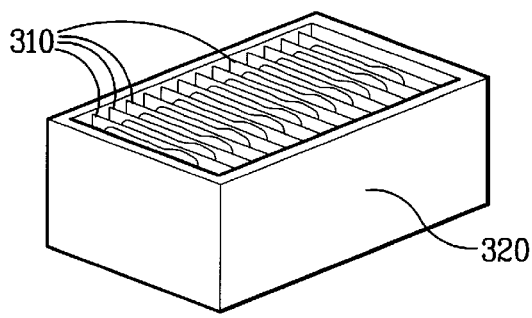
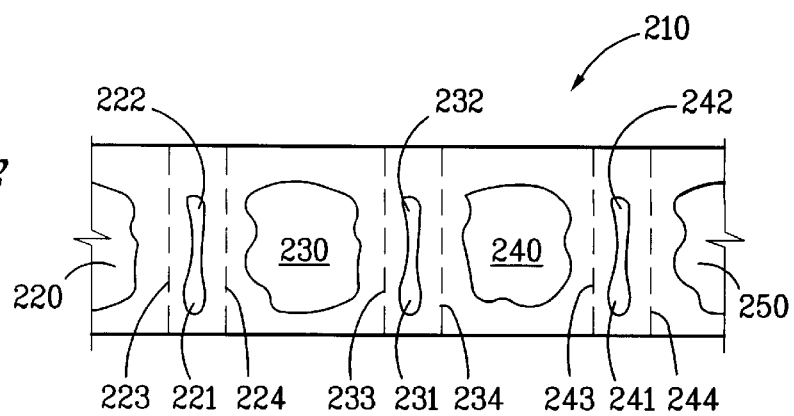

5,934,462

DURABLE GLOVE PACKAGES

BACKGROUND

The present invention relates to glove packages and more specifically to durable glove packages for sanitary storage of latex gloves.

Sanitary latex gloves are currently used by law enforcement officers, firemen, paramedics, rescue workers, and other security personnel in field operations. To avoid exposing gloves to the elements, such as heat, cold, and abrasion, law enforcement officers ordinarily keep the gloves in pouches on their duty belts, while paramedics tape the gloves together. Latex gloves deteriorate when exposed to elements such as air, clothing, or materials used to make pouches. Therefore, in order to be kept in a reasonable condition, latex gloves are usually stored in boxes, which normally contain large quantities of gloves. These boxes, however, are difficult to carry around. Furthermore, stored in large numbers in boxes, the gloves become contaminated and are no longer sanitary. Thus, because of the difficulty of carrying large boxes of gloves and because the gloves contained in large numbers therein are not sanitary, law enforcement and other security personnel are ordinarily deprived of the use of sanitary latex gloves during field operations. The problem solved by the present invention is providing pocket-sized individual glove packages for single-use application that are field-durable and are capable of being dispensed a single package at a time.

Various methods of storing sanitary latex gloves in individual glove packages are known in the prior art. Among these patents are U.S. Pat. No. 3,181,695 to Taterka et al., U.S. Pat. No. 3,107,786 to Adelman, and U.S. Pat. No. 4,951,815 to Ulbrich, all of which disclose sealed glove packages for storing folded-over gloves. Another related patent is U.S. Pat. No. 5,456,354 to Wood, for a package dispenser for dispensing latex gloves one at a time.

None of the above patents, however, solves the problem of providing pocket-sized durable glove packages containing sanitary latex gloves, capable of being dispensed a single package at a time for convenient use by law enforcement officers in the field. Thus, the glove packages known in the prior art are inapplicable for solving the present problem, in that they do not provide convenient-sized glove packages made of durable material for sanitary storage of latex gloves that are capable of being dispensed one package at a time for field use by law enforcement and other security personnel. There is a need, therefore, for a durable pocket-sized glove package containing sanitary gloves therein, having the capability of being dispensed one package at a time for convenient use by law enforcement personnel in field conditions. There are no known glove packages that are of convenient size and durable material which have the capability of being dispensed one at a time for convenient use by law enforcement officers and other security personnel during field operations.

SUMMARY OF THE INVENTION

The present invention alleviates to a great extent the above shortcomings in the prior art by providing durable pocket-sized glove packages that are capable of being dispensed one package at a time for convenient field use by law enforcement personnel. The glove packages in one aspect of the present invention are made of field-durable material capable of withstanding exposure to the elements, such as heat, cold, and abrasion, as well as enduring rough treatment by law enforcement officers in the field without, before being opened, compromising the sanitary condition of the gloves inside. Further, the glove packages are of convenient size for easy storage and transportation by law enforcement officers during field operations. The convenient size of the glove packages, representing one aspect of the present invention, may be effected, for example, by folding over the gloves at least once inside the packages so that the packages are of pocket size, suitable for carrying in pockets and pouches by law enforcement personnel. Thus, the present invention provides pocket-sized glove packages made of field-durable material for single-use application by law enforcement officers in the field.

In yet another aspect of the present invention, the glove packages are suitable for field use by law enforcement personnel because they are capable of being dispensed one package at a time, thus enabling users, such as law enforcement officers, to select and carry with them the number of packages they need for a single field operation. This dispensing feature may be effected, for example, by providing a glove package strip composed of removably connected durable pocket-sized glove packages for convenient use by law enforcement and other security personnel during field operations. An alternate embodiment of the present invention provides individual pocket-sized durable glove packages stored in a box or other container, capable of being dispensed one package at a time from that box or container, for convenient use by law enforcement and other security personnel during field operations.

It is thus an object of the invention to provide field-durable glove packages for convenient use by law enforcement personnel during field operations.

It is a further object of the invention to provide glove packages yielding the foregoing advantages and that are pocket-sized for convenient storage and transportation in pockets and pouches of users, such as law enforcement personnel.

It is a further object of the invention to provide glove packages yielding the foregoing advantages and that are individually dispensable to enable users, such as law enforcement officers, to select the number of packages they need for a single field operation.

It is yet another object of the invention to provide glove packages yielding the foregoing advantages and that are simple and easy to construct.

Other objects and advantages of the present invention will be readily apparent from the following description and drawings which illustrate the present invention.

BRIEF DESCRIPTION OF THE DRAWINGS

FIG. 1 shows glove packages according to a first preferred embodiment of the present invention.

FIG. 2 shows glove packages according to a second preferred embodiment of the present invention.

FIG. 3 shows glove packages according to a third preferred embodiment of the present invention.

DETAILED DESCRIPTION OF PREFERRED EMBODIMENTS

Referring to FIG. 1, there being shown a first preferred embodiment of the invention, the latex gloves 38 are separately packaged in individual packages 20, 30, and 40. Adjacent individual glove packages are connected to each other to form glove package strip 10. Perforations 25 and 35 extend along the width of glove package strip 10 between any two adjacent individual glove packages, thus separating the individual glove packages from one another. Individual glove packages 20, 30, and 40 are removably connected to one another by means of perforations 25 and 35. Perforations 25 and 35 permit each of the packages 20, 30, and 40 to be detached from glove package strip 10 at perforations 25 and 35.

Referring to individual glove package 30, shown in FIG. 1, the package includes a front sheet 37, a back sheet 36, and a border 39. Front sheet 37 includes an inside surface 131 and outside surface 132. Back sheet 36 includes an inside surface 133 and an outside surface 134. Border 39 is formed around the portion of glove package 30 containing gloves 38. Border 39 is formed by sealing together the ends 31 and 33 and the edges 32 and 34 of the inside surfaces 131 and 133 of front sheet 37 and back sheet 36. The ends 31 and 33 of border 39 extend along the rim of the glove package strip. The edges 32 and 34 of border 39 extend in proximity to perforations 35 and 25, which removably connect glove package 30 to glove packages 20 and 40. Border 39 of glove package 30 completely surrounds the portion of the package containing gloves 38. The central portion of the glove package 30 (containing the folded gloves 38) is substantially thicker than the sealed border 39.

The front sheet 37, back sheet 36, and border 39 of glove package 30 are composed of field-durable material. This field-durable material, such as foil or vinyl, should have the necessary toughness and thickness to withstand rough treatment by law enforcement officers, firemen, rescue workers, and other security personnel during field operations, without impairing the sanitary condition of the gloves contained therein. Additionally, the field-durable material should be able to withstand, depending on the conditions of its intended use, exposure to the elements, such as cold, heat, and abrasion, to which the packages may be exposed during specific field applications. Thus, depending on the application it is intended for, the field-durable material should be of specific composition and have sufficient toughness and thickness to withstand the field conditions it is designed to be used in. For example, the composition, toughness, and thickness of the field-durable material of glove packages intended for use by paramedics may be different from the composition, toughness, and thickness of the field-durable material intended for use by firemen. Needless to say, some field-durable materials will be suitable for a wide variety of applications.

The field-durable material, therefore, should be of the requisite composition, toughness, and thickness, depending on the intended application of the glove packages, so that the sanitary condition of the gloves contained inside the package will generally not be compromised before the package is opened. The field-durable material of the package should be such that the gloves inside should generally remain in sanitary condition until the package is opened, unless the package is exposed to extremely rough treatment by law enforcement officers or other security personnel or to severe conditions such as extreme temperatures.

Individual glove packages 20, 30, and 40 may be vacuum-sealed to preserve the sanitary condition of the gloves therein.

In the preferred embodiment of the invention shown in FIG. 1, latex glove 38 is folded over inside glove package 30 at least once to ensure that the size of the individual glove package is suitable for convenient storage in pockets, pouches, or bags, for use by law enforcement and other security personnel during field operations. These small-sized packages are easy to carry and transport, and the gloves contained therein are sanitary.

FIG. 2 illustrates a second preferred embodiment of the glove packages of the present invention. Unlike the first preferred embodiment of the invention shown in FIG. 1, where the glove packages are connected to each other to form a glove package strip, the glove packages shown in FIG. 2 are not connected to each other and are individually stored. Individual glove packages 310 are stored in dispensing container 320. Dispensing container 320 has the capability of dispensing a single glove package at a time, enabling law enforcement officers to select and carry with them the number of individual glove packages they need for any given field operation. As in the first preferred embodiment of the present invention shown in FIG. 1, individual glove packages 310 are made of field-durable material. Individual glove packages 310 are pocket-sized, for convenient storage and transportation by law enforcement officers and other security personnel during field operations.

FIG. 3 illustrates a third preferred embodiment of the glove packages of the present invention provided in the form of glove package strip 210. Sequential glove packages 220, 230, 240, and 250 are removably connected to each other by means of perforated portions 221, 231, and 241. Perforations 223, 224, 233, 234, 243, and 244 extend along the width of glove package strip 210, between adjacent glove packages and perforated portions. Perforated portions 221, 231, and 241 connect glove packages 220, 230, 240, and 250 to form glove package strip 210. Glove packages 220, 230, 240, and 250 may be detached from the glove package strip at perforations 223, 224, 233, 234, 243, and 244 for easy storage and transportation by law enforcement officers and other security personnel in the field. Perforated portions 221, 231, and 241 may facilitate carrying several glove packages without detaching the glove packages from the glove package strip. This is accomplished by folding the strip twice, at two perforations extending along both sides of a perforated portion, between any two sequential glove packages. Because of the thickness of the glove packages with the gloves inside, folding the glove package strip twice with the narrow perforated portion between sequential glove packages, allows the thus folded sequential glove packages to form a compact conveniently-sized packet for carrying in pockets, belts, and pouches of law enforcement officers. For example, glove package strip 210 can be folded twice along perforations 233 and 234 between glove packages 230 and 240 to form a compact packet for easy storage and transportation by users, such as law enforcement officers. In the absence of a perforated portion with two perforations extending along the width of the glove package strip between any two adjacent glove packages, the thickness of the adjacent glove packages would cause them to open wide if they are not detached from the strip, thus making them inconvenient for carrying as a compact-sized packet in pockets or pouches of law enforcement officers.

Further, in the third preferred embodiment of the invention shown in FIG. 3, perforated portions 221, 231, and 241 may contain a substance 222, 232, and 242 such as lubricant, gel, or powder to facilitate the donning of gloves or to serve a particular field-related function during use by law enforcement officers and other security personnel in specific field applications.

Glove packages 220, 230, 240, and 250 shown in FIG. 3 are made of field-durable material. The gloves inside glove packages 220, 230, 240, and 250 are folded over at least once to ensure pocket-size dimensions of the glove packages for easy storage, transportation and use by law enforcement officers and other security personnel in the field.

The above description and drawings are only illustrative of the preferred embodiments that achieve the objects, features, and advantages of the present invention and it is not intended that the present invention is limited thereto. Any modifications of the present invention which come within the spirit and scope of the following claims are considered part of the present invention.

What is claimed is new and desired to be secured by Letters Patent of the United States is:

1. A glove package system, comprising:

a first pocket-sized glove package for single-use application, said pocket-sized glove package being formed of a material that is durable, temperature-resistant, and abrasion-resistant, said pocket-sized glove package containing a plurality of first sanitary latex gloves, said latex gloves being folded over and sealed within said package, and wherein said pocket-sized glove package is adapted to be carried by a security person in a field operation; and wherein said pocket-sized glove package includes a sealed border surrounding said latex gloves, and wherein said glove package includes a central portion, said central portion being surrounded by said sealed border, said latex gloves being located within said central portion, and wherein said central portion is substantially thicker than said sealed border; and wherein said glove package system further comprises a second pocket-sized glove package, and a sanitary latex glove sealed within said second pocket-sized glove package, said first glove package and said second glove package being connected to each other; and wherein said first pocket-sized glove package includes a front sheet and a back sheet, said central portion being formed by said front sheet and said back sheet, said front sheet and said back sheet being formed of field-durable material, said front sheet being attached to said back sheet at said sealed border, and wherein said first sanitary latex gloves are not attached to said front sheet, said back sheet, and said sealed border of said first pocket-sized glove package.

2. The glove package system of claim 1, wherein said first glove package is vacuum-sealed.

3. The glove package system of claim 1, further comprising a perforated portion, said first glove package being connected to said second glove package by said perforated portion.

4. The glove package system of claim 3, further comprising a substance for treating gloves, said substance being located in said perforated portion.

5. The glove package system of claim 4, wherein said substance includes a lubricant.

6. The glove package system of claim 4, wherein said substance includes a powder.

7. The glove package system of claim 1, further comprising a dispensing container, said first and second glove packages being located in said container.

8. A glove package system, comprising:

a first pocket-sized glove package for single-use application, said pocket-sized glove package being formed of a material that is durable, temperature-resistant, and abrasion-resistant, said first pocket-sized glove package containing at least one latex glove, said latex glove including a main portion and finger portions extending from said main portion, said latex glove being folded over such that said finger portions are folded onto said main portion, such that said finger portions contact said main portion of said latex glove, and wherein said latex glove is sealed within said first pocket-sized glove package, and wherein said glove package is adapted to be carried by a security person in a field operation; and wherein said first pocket-sized glove package includes a sealed border surrounding said latex glove, and wherein said glove package includes a central portion, said central portion being surrounded by said sealed border, said latex glove being located within said central portion, and wherein said central portion is substantially thicker than said sealed border; and wherein said glove package system further comprises a second pocket-sized glove package, and a latex glove sealed within said second glove package, said first glove package and said second glove package being connected to each other; and wherein said first pocket-sized glove package includes a front sheet and a back sheet, said central portion being formed by said front sheet and said back sheet, said front sheet and said back sheet being formed of field-durable material, said front sheet being attached to said back sheet at said sealed border, and wherein said latex glove of said first glove package is not attached to said front sheet, said back sheet, and said sealed border of said first glove package.

9. The glove package system of claim 8, wherein said first glove package is vacuum-sealed.

10. The glove package system of claim 9, further comprising a perforated portion, said first glove package being connected to said second glove package by said perforated portion.

11. The glove package system of claim 10, further comprising a lubricant located in said perforated portion.

12. The glove package system of claim 9, further comprising a container, said first and second glove packages being located in said container.

13. The glove package system of claim 9, further comprising a second glove located in said first glove package.

* * * * *